(12) United States Patent
Jin

(10) Patent No.: US 8,524,976 B2
(45) Date of Patent: Sep. 3, 2013

(54) IDURONIDASE KNOCK-OUT MOUSE

(75) Inventor: Thong-Gyu Jin, Seoul (KR)

(73) Assignee: Medigenbio Corporation, Yongin, Gyeonggi-do (KR)

(*) Notice: Subject to any disclaimer, the term of this patent is extended or adjusted under 35 U.S.C. 154(b) by 0 days.

(21) Appl. No.: 12/585,544

(22) Filed: Sep. 17, 2009

(65) Prior Publication Data

US 2011/0067120 A1 Mar. 17, 2011

(51) Int. Cl.
*A01K 67/027* (2006.01)
*A01K 67/033* (2006.01)
*A01K 67/00* (2006.01)
*G01N 33/00* (2006.01)

(52) U.S. Cl.
USPC .............. 800/18; 800/3; 800/13; 800/14

(58) Field of Classification Search
None
See application file for complete search history.

(56) References Cited

U.S. PATENT DOCUMENTS 6,002,067 A * 12/1999 Clarke et al. .................... 800/18

OTHER PUBLICATIONS

Camassola et al. (2005) Nonviral in vivo gene transfer in the mucopolysaccharidosis I murine model. Journal of Inherited Metabolic Disease 28: 1035-1043.*
Clarke et al. (1997) Murine mucopolysaccharidosis type I: targeted disruption of the murine alpha-L-iduronidase gene. Human Molecular Genetics 6(4): 503-511.*
Liu et al. (2005) Liver-directed neonatal gene therapy prevents cardiac, bone, ear, and eye disease in mucopolysaccharidosis I mice. Molecular Therapy 11(1): 35-47.*
Ohmi et al. (2003) Activated microglia in cortex of mouse models of mucopolysaccharidoses I and IIIB. Proc. Natl. Acad. Sci. USA 100(4): 1902-1907.*
Itaya et al. (1989) A neomycin resistance gene cassette selectable in a single copy state in the *Bacillus subtilis* chromosome. Nucleic Acids Research 17(11): 4410.*
Clarke et al. (1997) Murine mucopolysaccharidosis type 1: targeted disruption of the murine alpha-L-iduronidase gene. Human Molecular Genetics 6(4): 503-511.*

* cited by examiner

*Primary Examiner* — Anne-Marie Falk
(74) *Attorney, Agent, or Firm* — Edwards Wildman Palmer LLP; Kongsik Kim

(57) ABSTRACT

The present invention relates to a α-L-iduronidase knock-out mouse. More particularly, this invention relates to a α-L-iduronidase knock-out mouse to be designed for developing a treatment or an agent for mucopolysaccharidosis type I (Hurler syndrome or Hurler-Scheie syndrome) as an animal model.

1 Claim, 7 Drawing Sheets

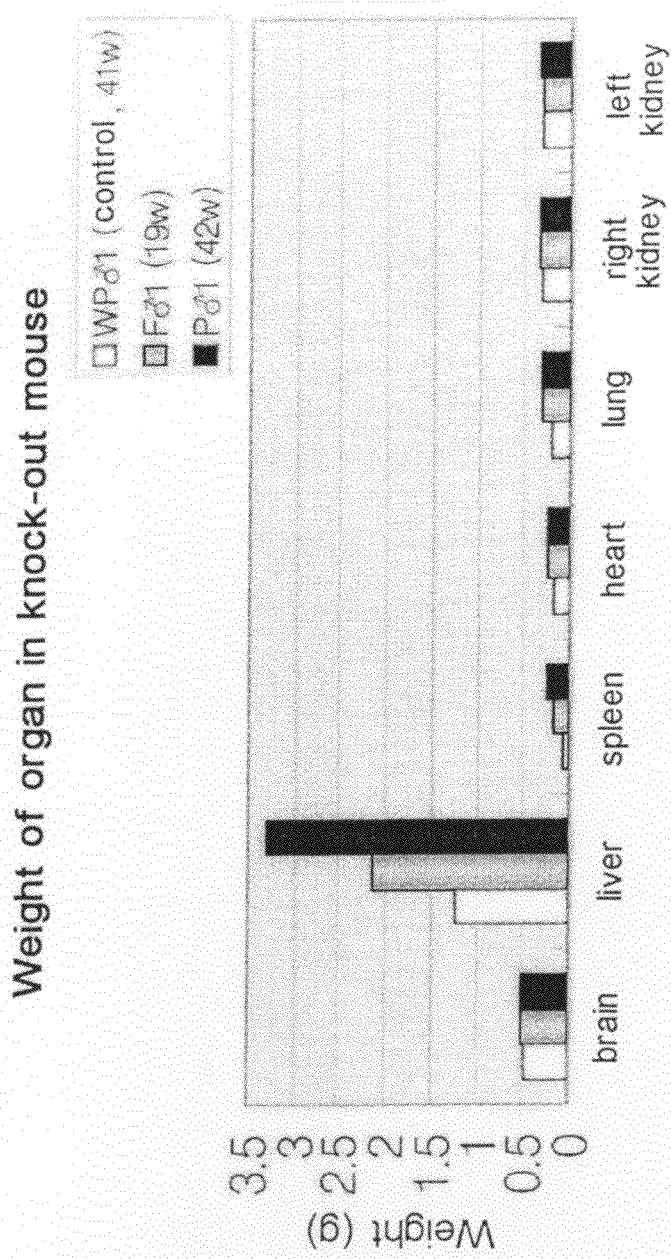

IDURONIDASE KNOCK-OUT MOUSE

BACKGROUND OF THE INVENTION

1. Field of the Invention

The present invention relates to a α-L-iduronidase knock-out mouse. More particularly, this invention relates to a α-L-iduronidase knock-out mouse to be designed for developing a treatment or an agent for mucopolysaccharidosis type I (Hurler syndrome or Hurler-Scheie syndrome) as an animal model.

2. Description of Prior Art

Mucopolysaccharidosis is a metabolic disorder caused by the absence or mal-function of lysosomal enzyme required for degenerating the glycosaminoglycan, one of long chain of sugar carbohydrates in the cell, which helps to build the bone, cartilage, tendon, cornea, skin and connective tissue.

Mucopolysaccharidosis (MPS) I can be classified into three sub-types based on severity of symptom. All three types result from the absent or insufficient levels of α-L-iduronidase enzyme (IDUA; mucopolysaccharide α-$_L$-iduronohydrolase; EC 3.2.1.76). Iduronidase is an enzyme involved in the degeneration of glycosaminoglycans, such as, dermatan sulfate and heparan sulfate, which are found in the lysosome in the cell. The defective α-L-iduronidase results in the accumulation of heparin and dermatin sulfate within phagocytes, endothelium, smooth muscle cells, neurons, and fibroblasts.

MPS I H is also called as Hurler syndrome, and it is the most severe syndrome of the MPS I sub-types. Delay of development is obvious by the end of the first year, and patient usually stops developing between ages 2 and 4. Further, progressive mental decline and loss of physical skills follow. Growth in height may be faster than normal, but begins to slow before the end of the first year. Then, the growth often ends around age 3.

MPS I S is also called as Scheie syndrome, and it is the mildest form of MPS I. Symptoms generally begin to appear after age 5, and diagnosis of this symptom can be made after age 10. Even though some of children having Scheie syndrome shows normal intelligence, others may have a mild learning disability and a psychiatric problem. The symptoms such as glaucoma, retinal degeneration, or clouded corneas may impair the vision of child.

MPS I H-S is also called as Hurler-Scheie syndrome, and it is less severe than Hurler syndrome. Symptoms generally begin between ages 3 and 8. Children may have moderate mental retardation and learning disability. Skeletal and systemic irregularities include short stature, marked smallness in the jaws, progressive joint stiffness, compressed spinal cord, clouded corneas, hearing loss, heart disease, coarse facial features, and umbilical hernia. Respiratory problems, sleep apnea, and heart disease may develop in adolescence.

To develop the agent for treating MPS I, knock-in mouse model for developing the agent has been designed. In U.S. Pat. No. 6,002,067, knock-in mouse which is homozygous for a disruption in the IDUA gene, but which has normal expression for the SAT-1 gene has been disclosed. In this disclosure, it has been also disclosed that knock-in mouse can be used for evaluating therapeutic agents in treating mucopolysaccharidosis Type I, by administering the therapeutic agent to the mouse, and evaluating the mouse for tissue pathology associated with iduronidase deficiency.

However, it has a doubt if knock-in mouse is the best model for evaluating the ability of a targeting system to deliver a therapeutic agent to selected tissues or organs by administering an effective iduronidase replacement therapy, because knock-in mouse has a possibility to show different pathophysiological characteristics of human iduronidase deficiency syndrome, such as, Hurler syndrome or Hurler-Scheie syndrome.

For treating a mucopolysaccharidosis (MPS) I, Genzyme Co., Ltd. has developed the enzyme of α-L-iduronidase as trademark of 'Aldurazyme' using CHO cell by genetic engineering method. In 2003, this enzyme drug has been approved for treating Hurler syndrome or Hurler-Scheie syndrome by FDA. Recently, this drug has been commercially marketed in about 20 countries.

Aldurazyme consists of 653 amino acids. In this enzyme, there are 6 N-linked oligosaccharide sites which are 110th residue, 190th residue, 336th residue, 372nd residue, 415th residue and 451st residue. Further, mannose 6-phosphate chain has been linked to 336th residue and 451st residue. Intracellular absorption of this enzyme has been made by the affinity between mannose 6-phosphate chain and mannose 6-phosphate receptor in the cell. Like other enzyme prepared by recombinant DNA method, Aldurazyme also has a handicap of absorption in the cells of patient.

Direct enzyme replacement method has been developed for administrating an Aldurazyme or its analogue for treating Hurler syndrome or Hurler-Scheie syndrome. Further, cell implant or gene therapy using vector also have been tried for treating Hurler syndrome or Hurler-Scheie syndrome. Any of treating methods developed until now cannot show the sufficient treating effect. Further, we cannot estimate which treating method will be effective to individual patient.

The present invention is to provide a knock-out mouse model for diagnosing or treating Hurler syndrome or Hurler-Scheie syndrome. For this purpose, the inventor has prepared α-L-iduronidase knock-out mouse, in which wild type of α-L-iduronidase gene has been replaced by knock-out targeted gene.

SUMMARY OF THE INVENTION

The object of present invention is to provide a knock-out mouse comprising disruption in the α-L-iduronidase gene, wherein said disruption has been introduced into its genome by homologous recombination with a DNA targeting construct in an embryonic stem cell such that the targeting construct is stably integrated in the genome of said mouse, wherein the disruption of the α-L-iduronidase gene results in an inability of said mouse to produce detectable levels of α-L-iduronidase.

Further, said DNA targeting construct comprises 2534 bp of left arm, 1300 bp of neomycin resistance gene (MC1-neo) and 7112 bp of right arm, wherein the left arm is constructed from 18550 residue to 21083 residue of normal α-L-iduronidase gene, the right arm is constructed from 22232 residue to 29343 residue of normal α-L-iduronidase gene.

Further, said neomycin resistance gene (MC1-neo) is flanked by LoxP sites where deletion part of α-L-iduronidase gene consists of 1150 bp from 21084 residue to 22231 residue.

Further, said DNA targeting construct deletes a part of exon 6, exon 7, exon 8 and a part of exon 9 from wild type of α-L-iduronidase gene.

The further object of present invention is to provide a method for screening a candidate agent for the ability to treat Hurler syndrome or Hurler-Scheie syndrome in knock-out mouse comprising:

(a) providing a first knock-out mouse and a second knock-out mouse;

(b) administering a candidate agent to first knock-out mouse, and (c) comparing Hurler syndrome or Hurler-Scheie syndrome of first knock-out mouse of step (b) with Hurler syndrome or Hurler-Scheie syndrome of second knock-out mouse of step (a) without being administered;

wherein first knock-out mouse administered with candidate agent reduces Hurler syndrome or Hurler-Scheie syndrome compared to second knock-out mouse without being administered with candidate agent.

BRIEF DESCRIPTION OF THE DRAWINGS

FIGS. 2-1 and 2-2 show the construction of targeting vector, named as pIdua-KO vector, for preparing α-L-iduronidase knock-out mouse. Said targeting vector consists of 2534 bp of left arm, 1300 bp of neomycin resistance gene (MC1-neo) and 7112 bp of right arm. The left arm is constructed from 18550 residue to 21083 residue of normal α-L-iduronidase gene. The right arm is constructed from 22232 residue to 29343 residue of normal α-L-iduronidase gene. The neomycin resistance gene (MC1-neo) is flanked by LoxP sites where deletion part of α-L-iduronidase gene consists of 1150 bp from 21084 residue to 22231 residue.

FIG. 3 shows the urine glycosaminoglycan (GAG) amount of homozygote and heterozygote knock-out mouse.

FIG. 4 shows the weight of organ of homozygote and heterozygote knock-out mouse.

DETAILED DESCRIPTION OF THE INVENTION

Figure 1:
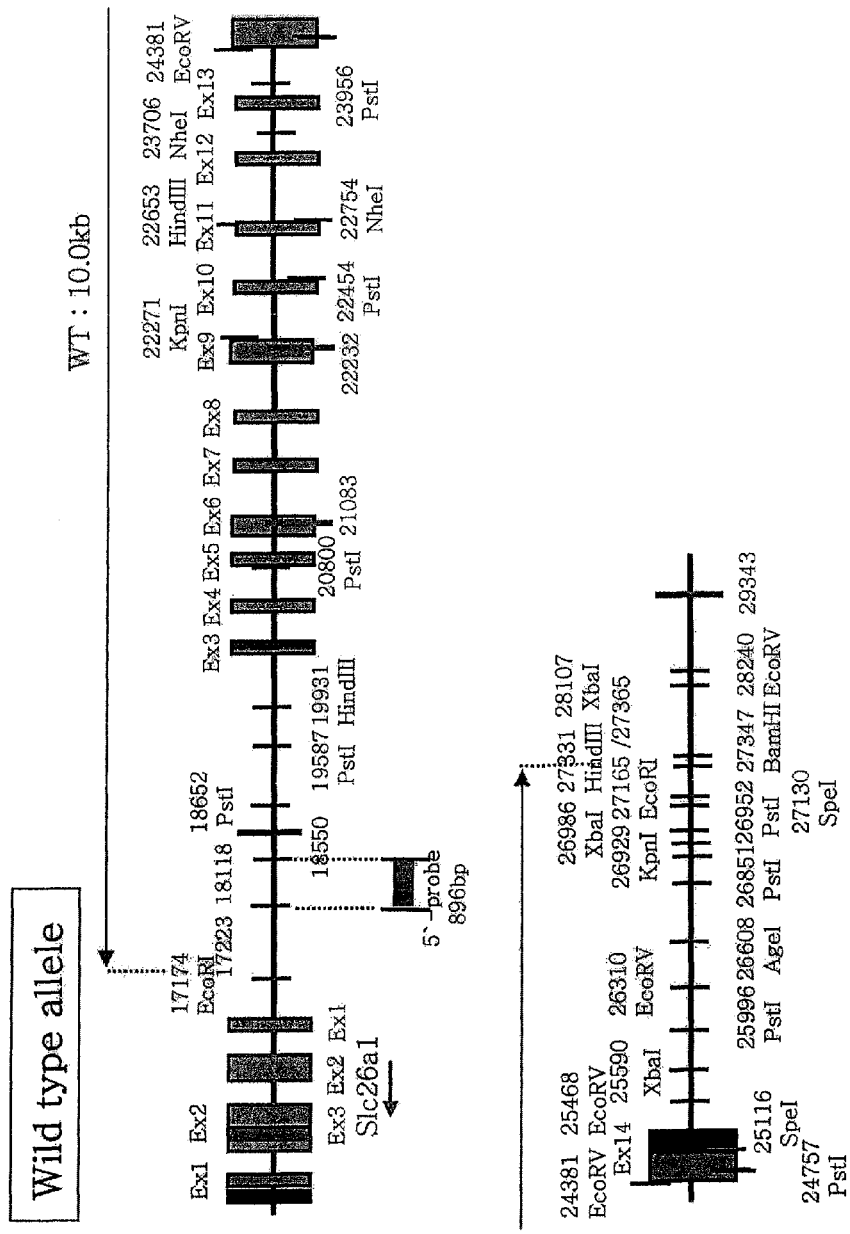
FIGS. 1-1, 1-2 and 1-3 show the targeted allele for preparing α-L-iduronidase knock-out mouse compared to the wild type allele of α-L-iduronidase gene of normal mouse. Wild type of α-L-iduronidase gene consists of 14 exons from exon 1 to exon 14, while targeted allele for preparing α-L-iduronidase knock-out mouse consists of exon 1, exon 2, exon 3, exon 4, exon 5, a part of exon 6, a part of exon 9, exon 10, exon 11, exon 12, exon 13 and exon 14. Therefore, targeted allele deletes a part of exon 6, exon 7, exon 8 and a part of exon 9 from wild type of α-L-iduronidase gene.
Figures 1, 2:
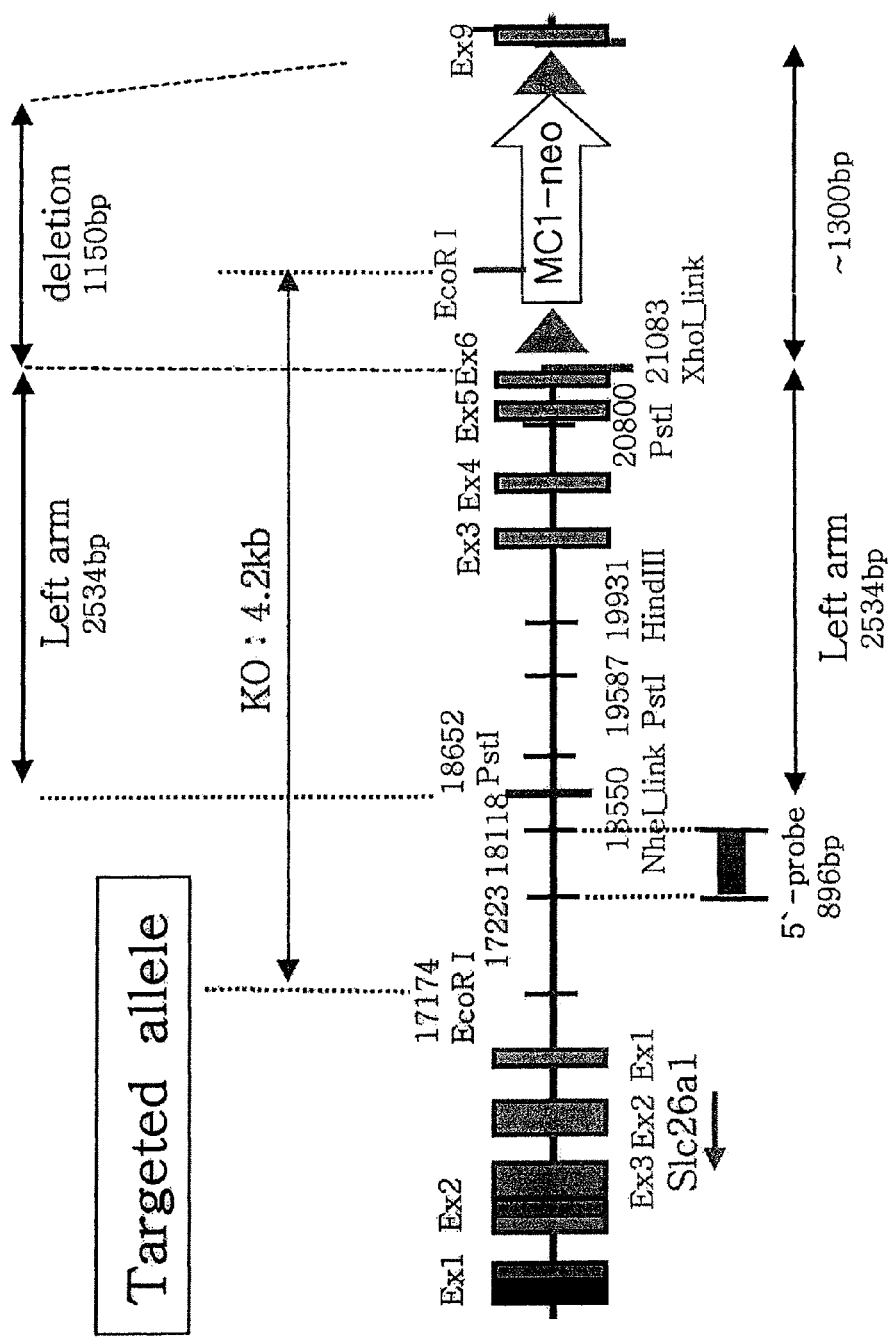
Figures 1, 2, 3:
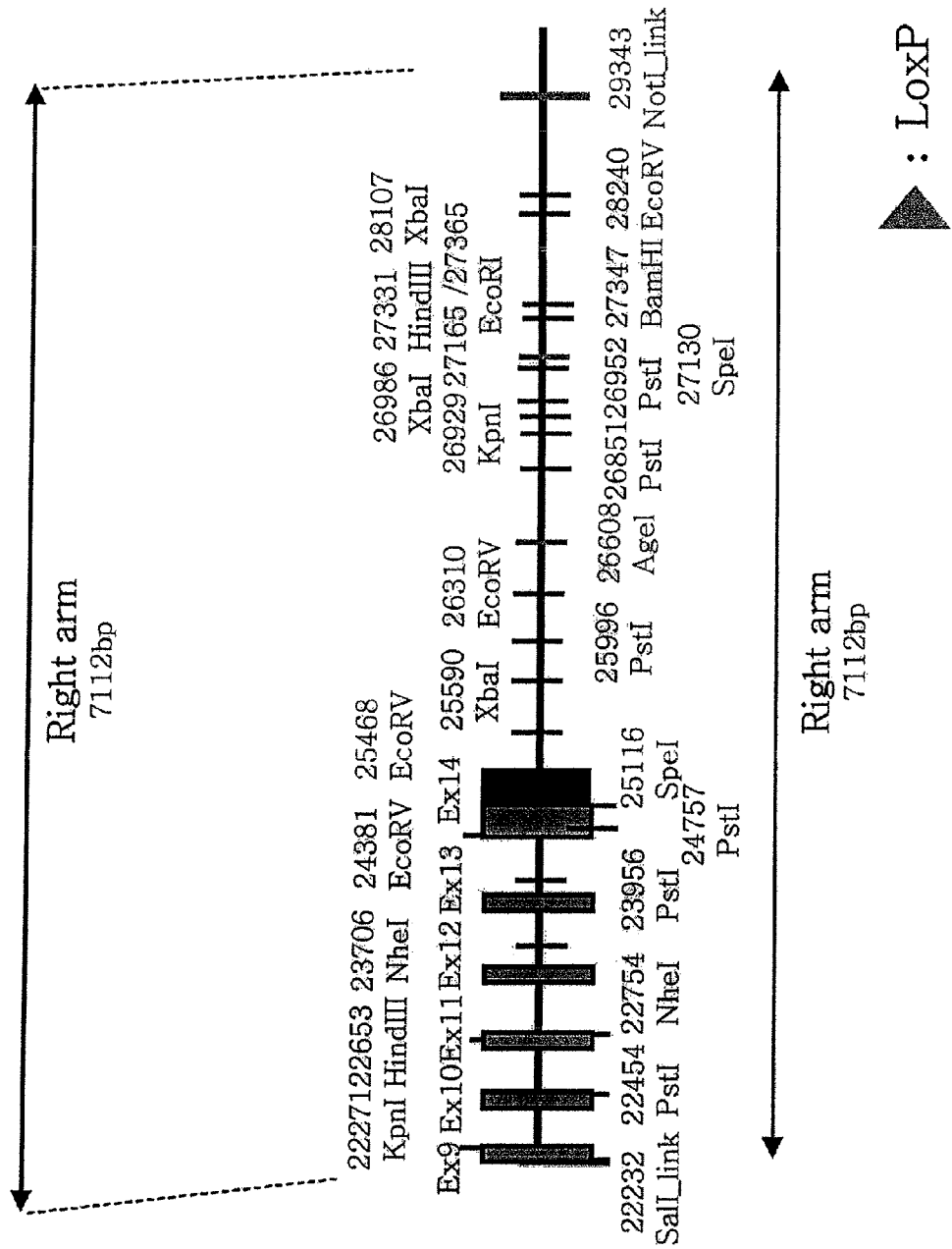
Figures 1, 2:
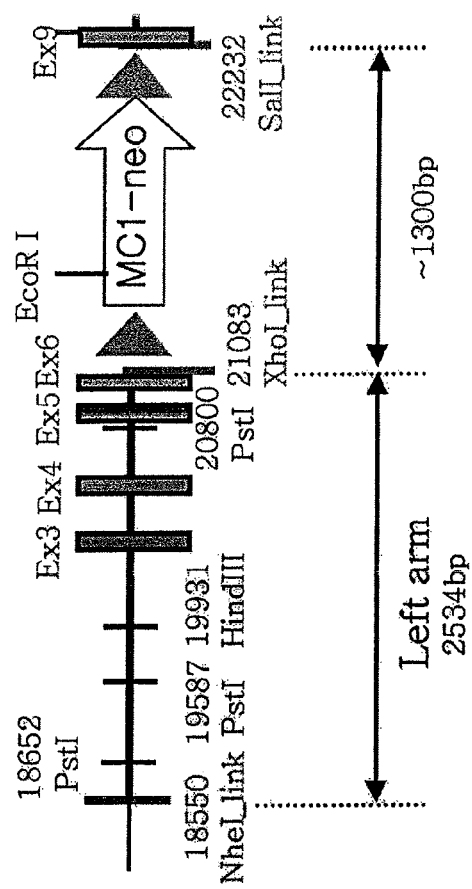
Figure 2:
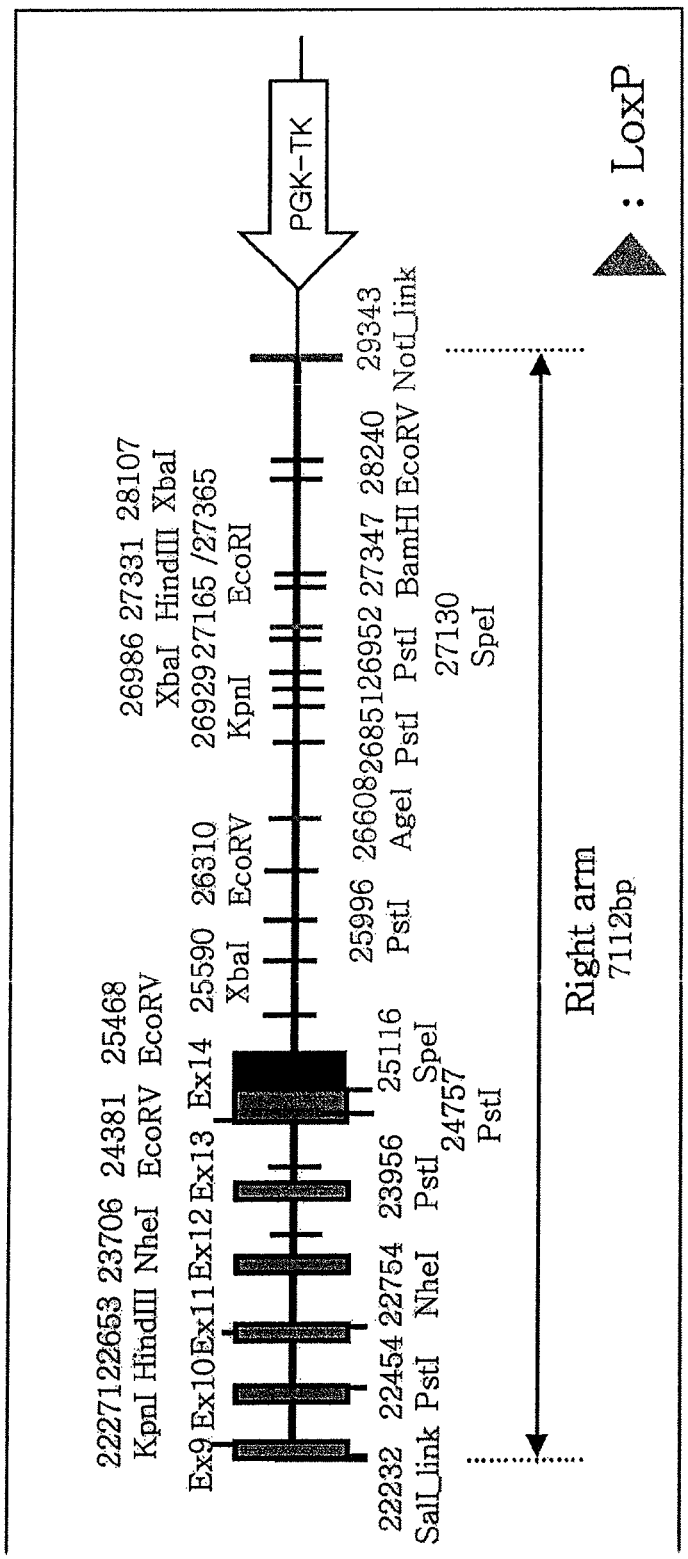
Figure 3:
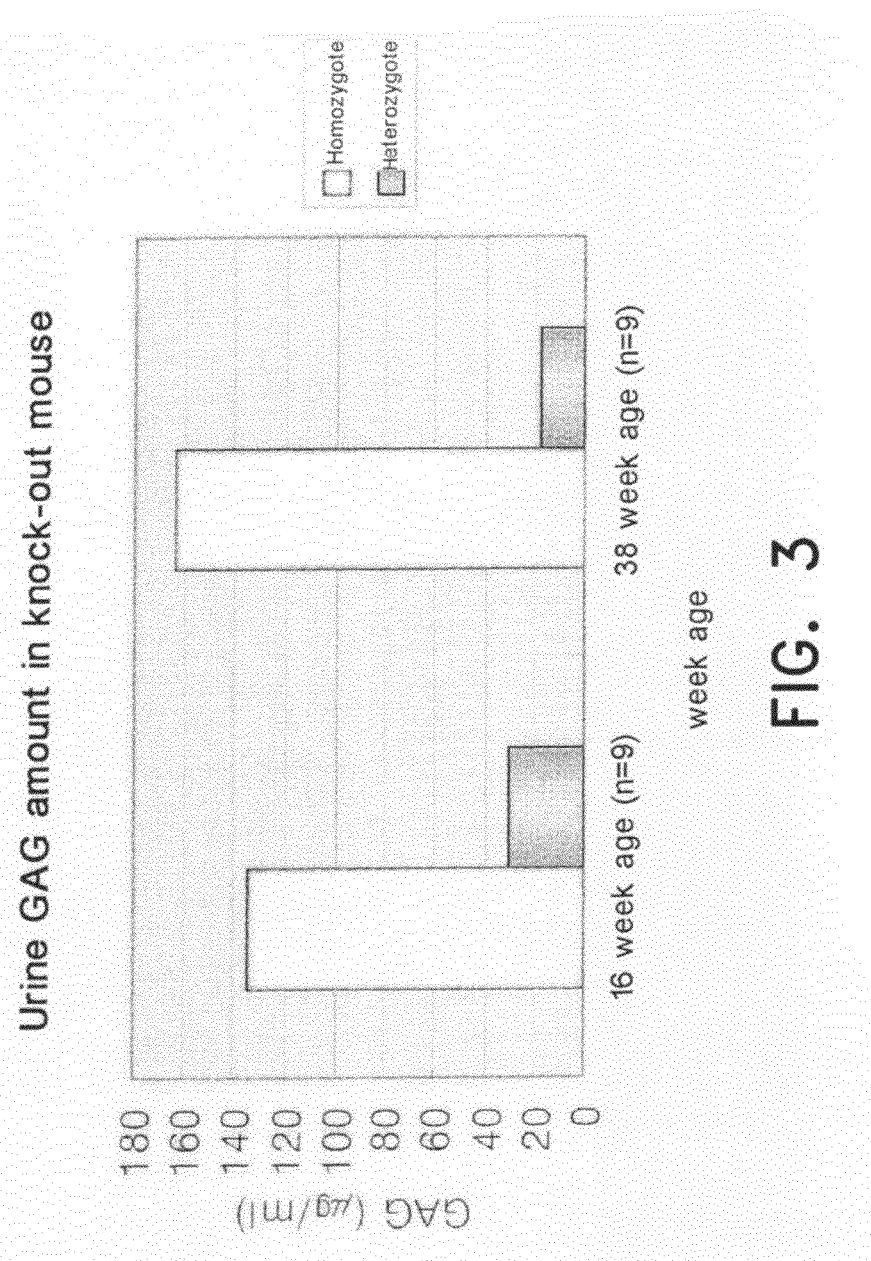

FIGS. 1-1, 1-2 and 1-3 show shows the targeted allele for preparing α-L-iduronidase knock-out mouse compared to the wild type allele of α-L-iduronidase gene of normal mouse. Wild type of α-L-iduronidase gene consists of 14 exons from exon 1 to exon 14, while targeted allele for preparing α-L-iduronidase knock-out mouse consists of exon 1, exon 2, exon 3, exon 4, exon 5, a part of exon 6, a part of exon 9, exon 10, exon 11, exon 12, exon 13 and exon 14. Therefore, targeted allele deletes a part of exon 6, exon 7, exon 8 and a part of exon 9 from wild type of α-L-iduronidase gene.

The gene fragment is obtained from a strain 129 mouse P1 genomic library that is screened using PCR primers corresponding to the coding region of the mouse α-L-iduronidase. Alternatively, such a fragment is obtained by probing a strain 129 genomic phage library with a mouse α-L-iduronidase cDNA probe using publically available sequences.

The Idua-KO construct is made by deleting a 1150 bp of α-L-iduronidase gene restriction fragment from the coding region of the α-L-iduronidase gene. The deleted region contains sequences encoding a region of the α-L-iduronidase protein consisting of a part of 6th exon, 7th exon, 8th exon and a part of 9th exon, more specifically 21084th residue to 22231st residue. In its place, a neomycin resistance cassette (MC1-neo) is inserted. The mutated fragment is subcloned into the pGK-TK plasmid, which contains the HSV thymidine kinase (TK) gene driven by the PGK promoter in a Bluescript vector.

FIGS. 2-1 and 2-2 show the construction of targeting vector, named as pIdua-KO vector, for preparing α-L-iduronidase knock-out mouse. Said targeting vector consists of 2534 bp of left arm, 1300 bp of neomycin resistance gene (MC1-neo) and 7112 bp of right arm. The left arm is constructed from 18550 residue to 21083 residue of normal α-L-iduronidase gene. The right arm is constructed from 22232 residue to 29343 residue of normal α-L-iduronidase gene. The neomycin resistance gene (MC1-neo) is flanked by LoxP sites where deletion part of α-L-iduronidase gene consists of 1150 bp from 21084 residue to 22231 residue.

Embryonic stem (ES) cells are electroporated with linearized pIdua-KO vector, and then plated on fibroblast feeder layers. ES cells are treated with geneticin (neomycin analog) to select for cells that had incorporated the targeting construct. ES cell clones surviving drug selection are screened for homologous recombination events by Southern blot analysis. In the process of constructing the pIdua-KO vector, an exogenous Xho I restriction site and Sal I restriction site are introduced at the 5' end of the Neo cassette and 3' end of the Neo cassette respectively. Therefore, ES cell genomic DNA is digested with Eco RI and DNA blots are hybridized with a probe corresponding to a .alpha.-L-iduronidase gene region located 5' and 3' to the integration site of the construct. With this strategy, the native allele is indicated by 10 Kb and a mutant allele by 4.2 Kb produced by homologous recombination are indicated.

A single clone of ES cells that had undergone homologous recombination is microinjected into blastocysts and 10 chimeric mice are generated. Six of the chimeras demonstrate 90% chimerism by color. Five chimeric males transmit the mutated allele through the germline. Heterozygote offspring are identified by both PCR and Southern analysis of genomic DNA. Heterozygotes exhibit a grossly normal phenotype and normal fertility. Genotyping 124 offspring from heterozygote crosses reveals the expected Mendelian ratios (+/+37/124, 29.8%; +/−54/124, 43.5% and −/−33/124, 26.6%) indicating no significant effect on embryo development.

The present invention also provides a method for screening a candidate agent for the ability to treat Hurler syndrome or Hurler-Scheie syndrome in the knock-out mouse comprising: (a) providing a first knock-out mouse and a second knock-out mouse; (b) administering a candidate agent to first mouse, and (c) comparing Hurler syndrome or Hurler-Scheie syndrome of first knock-out mouse of step (b) with Hurler syndrome or Hurler-Scheie syndrome of second knock-out mouse of step (a) without being administered; wherein first knock-out mouse administered with candidate agent reduces Hurler syndrome or Hurler-Scheie syndrome compared to second knock-out mouse without being administered with candidate agent.

Through use of the subject knock-out mouse, one can identify ligands or substrates that bind to, modulate, antagonize or agonize α-L-iduronidase. Screening to determine drugs that lack effect on this enzyme is also of interest. Areas of investigation are the development of treating Hurler syndrome or Hurler-Scheie syndrome. Of particular interest are screening assays for agents that have a low toxicity for human body.

A wide variety of assays may be used for this purpose including determination of the localization of drugs after administration, labeled in vitro protein-protein binding assays, protein-DNA binding assays, electrophoretic mobility shift assays, immunoassays for protein binding, and the like. Depending on the particular assay, whole knock-out mouse may be used.

The term "agent" as used herein describes any molecule including α-L-iduronidase, its analogue or its equivalent with the capability of affecting the biological action of α-L-iduronidase. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are enzymes. Candidate agents comprise functional groups necessary for structural interaction with enzymes, particularly hydrogen bonding, and typically include at least an amine, carbonyl, hydroxyl or carboxyl group, preferably at least two of the functional chemical groups.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries.

The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 1.0-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EXAMPLES

Following examples relates to pathophysiological characteristics of α-L-iduronidase knock-out mouse compared to that of wild type mouse.

Example 1

Urine Amount of GAG

FIG. 3 shows the urine glycosaminoglycan (GAG) amount of homozygote and heterozygote knock-out mouse. The urine amount of GAG of 38 weeks aged homozygote knock-out mouse is the range of 140-180 μg/ml. On the other hand, the urine amount of GAG of 38 weeks aged heterozygote knock-out mouse is the range of 10-30 μg/ml. Therefore, the urine amount of GAG of 38 weeks aged homozygote knock-out mouse is 5-20 fold of that of 38 weeks aged heterozygote knock-out mouse. It means that 38 weeks aged homozygote knock-out mouse cannot degenerate the GAG in the body, because 38 weeks aged homozygote knock-out mouse does not produce α-L-iduronidase in the body.

In case of 16 weeks aged knock-out mouse, the urine amount of GAG of 16 weeks aged homozygote knock-out mouse is the range of 120-140 μg/ml, while the urine amount of GAG of 16 weeks aged heterozygote knock-out mouse is the range of 20-40 μg/ml.

Example 2

Weight of Organ in Knock-Out Mouse

FIG. 4 shows the weight of organ of homozygote and heterozygote knock-out mouse. As shown in FIG. 4, the growth of liver has been extremely retarded in homozygote knock-out mouse. Further, the growth of spleens and lungs in homozygote knock-out mouse has been also retarded compared to those of heterozygote knock-out mouse.

Example 3

Histological Analysis of Liver and Kidney in Knock-Out Mouse

In the knock-out mouse liver and kidney, a lot of glycosaminoglycan (GAG) have been accumulated in lysosome of these organs. Further, the growth and development of these organs in homozygote knock-out mouse show to be retarded.

In case of liver, following pathological characteristics has been shown. Lysosome-laden Kupffer cells are readily found at 4 weeks of age with very little evidence of significant hepatocyte storage. By 10 weeks of age, further progression of storage within the reticuloendothelial system has occurred and there is now evidence of significant hepatocyte vacuolation. At this age 20 to 30% of the cytoplasm of the hepatocytes appear to be taken up by lysosomes, as contrasted to very few discernible lysosomes within normal liver samples.

What is claimed is:

1. A knock-out mouse comprising a disruption in the wild-type α-L-iduronidase gene,
wherein said disruption has been introduced into its genome by homologous recombination with a DNA targeting construct in an embryonic stem cell such that the targeting construct is stably integrated in the genome of said mouse,
wherein the disruption of the α-L-iduronidase gene results in an inability of said mouse to produce detectable levels of α-L-iduronidase;
wherein the disruption of said α-L-iduronidase gene results in a 1150 bp deletion consisting of a second part of exon 6, all of exon 7, all of exon 8 and a first part of exon 9;
wherein all of exons 1 to 5, a first part of exon 6, a second part of exon 9, and all of exons 10 to 14 are maintained in the genome; and
wherein the first part of exon 6 comprises the 5' end of exon 6, the second part of exon 6 comprises the 3' end of exon 6, the first part of exon 9 comprises the 5' end of exon 9, and the second part of exon 9 comprises the 3' end of exon 9.

* * * * *

UNITED STATES PATENT AND TRADEMARK OFFICE
CERTIFICATE OF CORRECTION

| | | |
|---|---|---|
| PATENT NO. | : 8,524,976 B2 | Page 1 of 1 |
| APPLICATION NO. | : 12/585544 | |
| DATED | : September 3, 2013 | |
| INVENTOR(S) | : Thong-Gyu Jin | |

It is certified that error appears in the above-identified patent and that said Letters Patent is hereby corrected as shown below:

Title page, item [73] assignee; should read as follows: "MediGeneBio Corporation"

Signed and Sealed this
Twenty-second Day of October, 2013

Teresa Stanek Rea
*Deputy Director of the United States Patent and Trademark Office*